(12) United States Patent
Monguillon et al.

(10) Patent No.: US 9,018,425 B2
(45) Date of Patent: Apr. 28, 2015

(54) USE OF SULFONIC ACID FOR RECOVERING GLYCEROL RESULTING FROM THE TRIGLYCERIDE TRANSESTERIFICATION REACTION

(71) Applicant: Arkema France, Colombes Cedex (FR)

(72) Inventors: Bernard Monguillon, Arbonnne (FR); Jean-Alex Laffitte, Pau (FR)

(73) Assignee: Arkema France, Colombes Cedex (FR)

( * ) Notice: Subject to any disclaimer, the term of this patent is extended or adjusted under 35 U.S.C. 154(b) by 0 days.

(21) Appl. No.: 14/198,251

(22) Filed: Mar. 5, 2014

(65) Prior Publication Data

US 2014/0256978 A1    Sep. 11, 2014

Related U.S. Application Data

(60) Provisional application No. 61/774,252, filed on Mar. 7, 2013.

(30) Foreign Application Priority Data

Mar. 6, 2013  (FR) ...................................... 13.51995
Dec. 3, 2013  (FR) ...................................... 13.61970

(51) Int. Cl.
| | | |
|---|---|---|
| *C07C 29/147* | (2006.01) | |
| *C07C 29/09* | (2006.01) | |
| *C07C 67/03* | (2006.01) | |
| *C11C 3/00* | (2006.01) | |
| *C07C 29/88* | (2006.01) | |

(52) U.S. Cl.
CPC ............... *C07C 29/095* (2013.01); *C07C 67/03* (2013.01); *C11C 3/003* (2013.01); *C07C 29/88* (2013.01)

(58) Field of Classification Search
USPC ........................... 568/869; 554/167, 169, 174
See application file for complete search history.

(56) References Cited

U.S. PATENT DOCUMENTS

| | | |
|---|---|---|
| 5,434,279 A | 7/1995 | Wimmer |
| 8,088,183 B2 | 1/2012 | Jackam et al. |
| 2010/0186289 A1 | 7/2010 | Bradin et al. |
| 2011/0245521 A1 | 10/2011 | Fassbender |
| 2012/0245371 A1 | 9/2012 | Lourenco et al. |

FOREIGN PATENT DOCUMENTS

| | | |
|---|---|---|
| CN | 101423456 A | 5/2009 |
| CN | 101475444 A | 7/2009 |
| EP | 0 658 183 B1 | 3/1997 |
| EP | 1 889 899 A1 | 2/2008 |
| FR | 2929621 A1 | 10/2009 |

*Primary Examiner* — Sikarl Witherspoon
(74) *Attorney, Agent, or Firm* — Smith, Gambrell & Russell, LLP

(57) ABSTRACT

The present invention relates to the use of at least one sulfonic acid for recovering glycerol resulting from a reaction crude from transesterification of glycerides, in particular of triglycerides of vegetable and/or animal origin.
The invention also relates to a process for purifying glycerol obtained as a by-product of triglyceride transesterification during the preparation of fatty acids, fatty esters and/or fatty acid salts, and also to a combined process for preparing, on the one hand, fatty acids, fatty esters and/or fatty acid salts and, on the other hand, glycerol, from triglycerides, using at least one sulfonic acid.

25 Claims, No Drawings

USE OF SULFONIC ACID FOR RECOVERING GLYCEROL RESULTING FROM THE TRIGLYCERIDE TRANSESTERIFICATION REACTION

The present invention relates to the use of sulfonic acid for preparing glycerol. More specifically, the present invention relates to a process for purifying glycerol obtained as a by-product of triglyceride transesterification during the preparation of fatty acids, of fatty esters and/or of fatty acid salts. This invention thus makes it possible to exploit the glycerol derived from the transesterification of triglycerides. The invention also relates to a combined process for preparing fatty acid esters and glycerol from glycerides using at least one sulfonic acid.

The triglycerides are predominantly triesters of glycerol and of fatty acids (they can also contain monoglycerides and diglycerides) and are found in abundance in nature, for example in oleaginous plants and animal fats, to mention only the most significant sources of triglycerides. There are today a very large number of industries carrying out the transesterification of these natural products which are triglycerides.

Among these industries, mention may be made, by way of non-limiting indication, of the industries for manufacturing cosmetic products, perfumes and fragrances, organic solvents, biodiesel, soaps, and the like.

The general reaction for triglyceride transesterification, generally carried out in a basic medium, in the presence of an alcohol, for example methanol, so as to give the corresponding fatty acid methyl esters, corresponds to the following scheme:

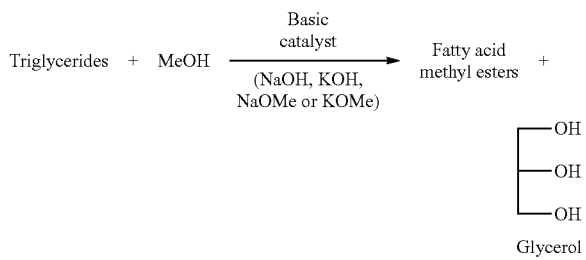

This transesterification reaction, which can be carried out relatively easily in the laboratory, exhibits, however, some difficulties from an industrial point of view. This is because the starting triglycerides usually contain a variable amount of free fatty acids (FFAs).

When this content of free fatty acids in the triglycerides is relatively high, typically greater than approximately 5% by weight, the FFAs can then form, in the presence of the basic catalyst, fatty acid salts which act as surfactants and cause foams that make it difficult to separate the glycerol from the fatty acid methyl esters formed.

This problem has been solved, and it is now known practice to carry out a pretreatment of the triglycerides, which consists of a first esterification of said FFAs in the presence of methanol and of an acid catalyst, such as sulfuric acid or methane sulfonic acid (cf. FR2929621). The FFAs previously contained in the triglycerides are then in the form of esters which will not be salified by the basic catalyst during the transesterification reaction.

The FFAs present in the starting triglycerides may also be in lower amounts, typically between 0.1% by weight and 5% by weight, and in this case, basic washing may be sufficient to remove them in the form of basic salts.

After the transesterification reaction, the fatty acid esters, generally fatty acid methyl esters, are present in the basic reaction medium with the glycerol. This reaction medium can comprise larger or smaller amounts of water depending on the conditions under which the transesterification reaction was carried out. The glycerol and also any water are not soluble in the fatty acid esters and are separated from the latter by decanting or any other means for phase separation.

The demand for fatty acid esters is constantly increasing, if only for the manufacture of biodiesel, and the industry today produces, and will even more so produce in the future, ever increasing amounts of these esters. The production of glycerol is consequently ever increasing and it would be entirely advantageous to be able to more successfully exploit this "by-product", with the objective of achieving a very high degree of purity, for example of pharmaceutical quality.

The prior art thus comprises a very large number of documents concerning the preparation of fatty acid esters, in particular for the production of biodiesel, via triglyceride transesterification reaction, as, for example, described in patent EP-B-0 658 183. More recently, application US 2011/0245521, which also relates to the production of biodiesel, only mentions very briefly the recovery of glycerol by chemical purification and distillation for use as an industrial or pharmaceutical raw material. No indication is provided with regard to said chemical purification and the distillation of the glycerol considered to be a "by-product".

Other prior art documents already relate to the possibility of exploiting glycerol, for instance patent application CN101423456, which describes a process for recovering and purifying glycerol as a by-product of biodiesel production. This purification uses molecular distillation to obtain a medical-quality glycerol. Such distillation of glycerol is carried out after the addition of sulfuric acid to the transesterification reaction medium.

As another example, patent application CN101475444 also describes a process for purifying glycerol resulting from the preparation of biodiesel which consists in filtering the crude glycerol so as to remove the solid impurities, in evaporating the filtered glycerol, and in introducing it into an ion exchange column and then, finally, subjecting it to thin-film distillation. The glycerol is obtained with a purity of more than 95%.

The prior art clearly teaches that the crude glycerol resulting from the transesterification of triglycerides is present in a basic phase which contains a more or less large amount of the surplus of alcohol used for the transesterification reaction (generally methanol), which may equally contain water, but also and especially residues of basic catalysts such as, for example, sodium hydroxide, potassium hydroxide, sodium methoxide or potassium methoxide, sodium or potassium salts of fatty acids, and also other impurities.

In addition, it is necessary to acidify this basic phase, in order to be able to isolate a glycerol of suitable purity. This is because sodium and/or potassium salts of fatty acids (often called "soaps") are in particular responsible for the formation of more or less substantial foams, thus creating an unwanted emulsion during the recovery of the alcohol (methanol) by evaporation, which makes it difficult to carry out this operation without losses in terms of yield and purity.

One of the advantages of this acidification operation is the conversion of these soaps into non-surfactant, free fatty acids which can then be separated much more easily from the glycerol phase, thus making it possible to subsequently exploit the latter under good conditions of purity and yield.

This acidification operation is generally carried out by adding at least one strong acid, generally in the form of an aqueous solution. The strong acids normally used are sulfuric acid, hydrochloric acid and phosphoric acid, which generate, respectively, sodium or potassium sulfates, chlorides and phosphates. However, each of these acids has drawbacks, in terms of corrosion, or of generation of effluents that are harmful to the environment, to mention only some of these drawbacks.

What is more, the presence of these salts (sulfates, chlorides and phosphates) in reality proves to be a great hindrance in several respects during the purification of the glycerol, quite particularly during its subsequent distillation. Indeed, it has been possible to observe that the sulfates, chlorides and phosphates have low solubility in glycerol and glycerol/water mixtures. This observed low solubility can be detrimental to the conducting of the distillation and the recovery of purified glycerol under acceptable yield and purity conditions.

The presence of insoluble compounds in the streams of an industrial distillation apparatus is highly prejudicial in that these insoluble compounds can cause disruption of the streams, in particular in the distillation column itself and can, consequently, lead to pressure drops, or even risks of clogging, deposits, etc. Furthermore, any pressure drop requires a greater energy consumption, in particular requires operating at a higher temperature, which results in degradation and decomposition of the product, thus leading to a loss of quality of the purified glycerol and overall distillation yield losses.

Application EP 1 889 899 A1 discloses a process for producing biodiesel also comprising a glycerol recovery step, in which the crude glycerol is acidified with an acid, preferably a weak organic acid, such as acetic acid, formic acid or propionic acid. The use of an organic acid does not result, according to said document, in the formation of insoluble salts. It is indicated that the crude glycerol must be acidified to a pH of less than 8, preferably between 6.5 and approximately 7.

Similarly, application US 2012/0245371 proposes a process for purifying crude alkaline glycerol obtained as a by-product during the manufacture of biodiesel from the transesterification reaction of vegetable oils and animal fats. This process comprises the acidification of the crude glycerol to a pH value of from approximately 4 to approximately 6 with an organic alkyl carboxylic acid, in the presence of water, acetic acid being the only representative exemplified. It is indicated in said application that the acidification with acetic acid does not cause the formation of solids above the glycerol phase.

The two documents previously mentioned thus teach that one of the problems encountered during the purification of an alkaline glycerol crude is the presence of insoluble salts which form during the neutralization or the acidification of the crude glycerol. This problem appears to be solved by using a weak acid, acetic, formic or propionic acid and in particular acetic acid, rather than a strong inorganic acid, such as hydrochloric, sulfuric or phosphoric acid.

However, the use of these weak acids ($pK_a$ greater than 3.5) does not allow sufficient acidification of the species present in the crude glycerol, in other words does not make it possible to reach a sufficiently low pH value to enable effective removal of soaps (in particular alkali metal salts of fatty acids) by converting them into free fatty acids, and sufficient solubilization of the other possible salts and impurities present in the crude glycerol.

In addition, the prior art shows that the use of these weak acids is accompanied by the addition of more or less large amounts of water, thus requiring the management of large stream volumes and the subsequent treatment of large amounts of effluents.

There remains therefore a need to improve the process for recovering crude glycerol obtained during transesterification reactions of glycerides, in particular natural glycerides, and more particularly glycerides used in the preparation of biodiesel.

The inventors have now discovered that the technical problems set out above can be totally, or at least partially, solved by virtue of the present invention. Thus, a first objective of the present invention consists in providing an improved process for recovering purified glycerol originating from a reaction crude resulting from the transesterification of glycerides, in particular natural glycerides, and more particularly glycerides used for the preparation of biodiesel.

Another objective consists in providing an improved process for recovering glycerol originating from a reaction crude resulting from the transesterification of glycerides, in which the operation of intermediate distillation of the methanol and/or water and final distillation of the glycerol is not disrupted by significant foaming in the distillation reboiler, and in which the stream and effluent volumes are entirely acceptable for industrial production of highly pure glycerol. Other further objectives will emerge in the disclosure of the present invention which follows.

The inventors have discovered, entirely surprisingly, that these objectives can be achieved, totally, or at least partially, by virtue of the process of the invention. This process comprises a step of acidification with at least one sulfonic acid which has the advantage of allying the properties of strong acids and of weak acids which are required for this process, i.e. allowing sufficient acidification to eliminate the risk of foam formation, and allowing the formation of soluble salts in order to eliminate the risks of clogging during the distillation operation. The use of at least one sulfonic acid represents an entirely unexpected and advantageous compromise for the industrial exploitation of glycerol resulting from triglyceride transesterification.

It has thus been discovered, surprisingly, that sulfonates, in particular alkane sulfonates, and more particularly methane sulfonates of alkali metals and alkaline-earth metals are more soluble in glycerol and glycerol/water mixtures than the other alkali metal and alkaline-earth metal salts formed from other strong acids, and in particular sulfuric acid, hydrochloric acid and phosphoric acid.

Thus, and according to a first aspect, the present invention relates to the use of at least one sulfonic acid, preferably at least one alkane sulfonic acid, for the recovery of glycerol resulting from a reaction crude from transesterification of glycerides, in particular of glycerides of vegetable and/or animal origin.

In the present invention, the term "sulfonic acid" is intended to mean the acids of general formula R—SO$_3$H, where R represents an alkyl or aryl radical, preferably an alkyl radical, and in the latter case the term alkane sulfonic acids is used. The alkane sulfonic acids preferred for the needs of the present invention are the acids of formula R—SO$_3$H, where R represents a linear or branched, saturated hydrocarbon-based chain containing from 1 to 4 carbon atoms.

The alkane sulfonic acids usable in the context of the present invention are particularly chosen from methane sulfonic acid, ethane sulfonic acid, n-propane sulfonic acid, iso-propane sulfonic acid, n-butane sulfonic acid, iso-butane sulfonic acid, sec-butane sulfonic acid, tert-butane sulfonic acid, and mixtures of two or more of them in any proportions.

The $pK_a$ values of the sulfonic acids, in general, and alkane sulfonic acids in particular, are all less than zero, whereas the $pK_a$ values of the alkylcarboxylic acids are all greater than 3.5. These acids, with $pK_a$ values greater than 3.5, are not sufficiently strong to ensure total acidification of all the species present in the medium.

According to one most particularly preferred embodiment, the alkane sulfonic acid used in the context of the present invention is methane sulfonic acid or ethane sulfonic acid; entirely preferably, the acid used is methane sulfonic acid of formula $CH_3SO_3H$.

Thus, the use according to the present invention employs at least one alkane sulfonic acid chosen from linear-chain or branched-chain alkane sulfonic acids containing from 1 to 4 carbon atoms, and preferably at least methane sulfonic acid (MSA).

Any type of formulation comprising at least one sulfonic acid, preferably alkane sulfonic acid, may be suitable. It is for instance thus possible to use at least one sulfonic acid in anhydrous form or in the form of an aqueous solution. As a general rule, the formulation comprises from 1% to 10% by weight of sulfonic acid(s), more generally from 5% to 90% by weight, in particular from 10% to 80% by weight of sulfonic acids, and more particularly from 15% to 75% by weight, the rest to 100% generally consisting of water. It goes without saying that, when the formulation comprises 100% by weight of sulfonic acid(s), this means that the sulfonic acid(s) is (are) used pure, more specifically used alone, without the addition of other formulation constituents.

The formulation is, for example, an aqueous formulation which can be prepared in the form of a concentrated mixture which is diluted by the final user. As a variant, the formulation can also be a ready-to-use formulation, i.e., a formulation which does not need to be diluted. Use may, for example, be made of methane sulfonic acid in an aqueous solution, sold by the company Arkema, for example an aqueous solution of methane sulfonic acid at 70% by weight in water, or else anhydrous methane sulfonic acid or AMSA.

The inventors have discovered that the sulfonates of alkali metals and alkaline-earth metals, in particular sodium and potassium methane sulfonates, are more soluble in glycerol or glycerol/water mixtures than the sulfate, chloride or phosphate salts of these same cations in this same medium.

According to one preferred embodiment, the present invention relates to the use, for recovering glycerol resulting from a glyceride transesterification reaction, of methane sulfonic acid (MSA) in any possible concentrations, ranging from AMSA (anhydrous MSA) to concentrations of about 5% by weight of MSA in water, and in particular the aqueous solutions of MSA at 70% by weight in water, sold by the company Arkema.

Another advantage associated with the use of a strong acid, and in particular a sulfonic acid, preferably alkane sulfonic acid, more preferably methane sulfonic acid, lies in the fact that the addition of such an acid makes it possible to reduce the viscosity of the glycerol-rich medium and to facilitate pH measurements. This is because, in the presence of water, strong acids, unlike "weak" organic acids, more readily confer a hydrophilic nature on the medium, consequently allowing better dissociation of the salts, thus facilitating pH measurements. In addition, reducing the viscosity of the medium, glycerol being a product with a relatively high viscosity, makes it possible to very substantially improve the separation, on the one hand, of the aqueous phase and, on the other hand, of the glycerol phase, for example through distillation, when necessary.

The term "reaction crude" comprising the glycerol that it is desired to recover is intended to mean the basic medium which constitutes the phase containing the glycerol after separation of the phase containing the fatty acid esters, the whole of the two phases resulting from the glyceride transesterification reaction, as described, for example, in applications EP 1 889 899 and US 2010/0186289.

Thus, the reaction crude, or crude reaction medium, is a basic mixture, with a pH generally between 10 and 14, and which typically comprises, for example:
   glycerol,
   the alcohol(s) used for the transesterification reaction,
   optionally water, or traces of water,
   the basic catalyst(s) (used for the transesterification reaction), possibly in trace form,
   fatty acid salt(s), possibly in trace form,
   optionally one or more fatty acid ester(s), possibly in trace form,
   optionally traces of mono-, di- and/or triglycerides,
   optionally traces of organic residues other than glycerol,
   optionally traces of metals.

The term "traces" is intended to mean amounts generally between a few ppm (weight) and 5% by weight relative to the total weight of the reaction crude, preferably between a few ppm (weight) and 2% by weight relative to the total weight of the reaction crude, entirely preferably between a few ppm (weight) and 1% by weight relative to the total weight of the reaction crude.

Among the basic catalysts which are present, possibly in the form of traces in the reaction crude, mention may be made of all the catalysts that can be used for glyceride transesterification reactions and in particular triglyceride transesterifications. Preferably, these basic catalysts are chosen from oxides, hydrides, hydroxides, carbonates, hydrogen carbonates, acetates and other alkoxides of alkali metals and alkaline-earth metals, the alkoxides originating from alcohols preferably containing from 1 to 5 carbon atoms. Among the basic catalysts, sodium hydroxide, potassium hydroxide, sodium alkoxides and potassium alkoxides are preferred. Entirely preferably, the basic catalysts are chosen from sodium hydroxide, potassium hydroxide, sodium methoxide and potassium methoxide, the latter two alkoxides being quite particularly preferred.

The expression "alcohol used for the transesterification reaction" is intended to mean, in general and by way of indicative but non-limiting examples, alcohols comprising from 1 to 10 carbon atoms, and preferably those chosen from methanol, ethanol, n-propanol, iso-propanol, n-butanol, iso-butanol, 3-methyl-1-butanol, neo-pentyl alcohol, pentanol and its isomers, hexanol and its isomers, heptanal and its isomers, octanol and its isomers, nonanol and its isomers, decanol and its isomers, and also mixtures of two or more of them in any proportions. Among the alcohols mentioned above, preference is given to methanol and ethanol, and particularly preferably to methanol.

The term "fatty acid salts" is intended to mean the alkali metal or alkaline-earth metal salts, preferably sodium salts and/or potassium salts, of the fatty acids resulting from the glyceride transesterification reaction and which can be found in trace amounts in the glycerol phase after the step of separating, on the one hand, the glycerol phase and, on the other hand, the fatty acid ester phase.

Likewise, traces of mono-, di- and triglycerides may be present in the glycerol phase, in particular when the transesterification reaction was carried out partially.

Likewise, one or more fatty acid ester(s) may be present in the basic reaction crude containing predominantly glycerol. These esters may be present in the glycerol phase for example because of their partial solubility in this phase, because of insufficient decanting, because of poor separation of the two phases, and the like.

The basic glycerol crude may also contain traces of organic residues originating from the starting oils before transesterification or else obtained as by-products of degradation during said transesterification reaction. The starting oils subjected to transesterification may also contain traces of metals, it being possible for the latter to also be introduced by the catalysts employed, the water or else the alcohol used.

Finally, water may be present, in trace amounts or in larger amounts. Traces of water may in fact be present in the triglycerides used in the transesterification reaction, but also and especially the water may be introduced in particular by the basic catalyst, for example when the latter is sodium hydroxide or potassium hydroxide in the form of an aqueous solution.

The glycerol phase thus comprises, in addition to the glycerol of interest that it is desired to recover, numerous other impurities, some of which may be present in the solid state. According to one preferred embodiment, these solid impurities are separated according to any separation means known to those skilled in the art, for example physical separation, such as centrifugation and/or filtration.

As previously indicated, this glycerol phase is basic, owing to the basic catalyst(s) used during the transesterification reaction, and it is advisable to acidify this basic phase, in order to bring its pH to a value strictly below 4, preferably below 3, for example to a pH value close to 2.

To this effect, and according to the use of the present invention, at least one sulfonic acid, and preferably methane sulfonic acid, is added to said reaction crude before carrying out a distillation reaction aimed at recovering the glycerol contained in said reaction crude, from which solid elements present therein have optionally, but preferably, been removed as previously indicated.

The amount of sulfonic acid(s) introduced into the reaction crude can therefore vary in large proportions according to the various basic elements present in said reaction crude. Those skilled in the art will know how to adjust the amount of sulfonic acid(s) to be added to the reaction crude according also to the concentration of said acid(s). According to one embodiment, the addition of acid is carried out with stirring and the pH of the solution is continuously checked. The addition of acid(s) is then stopped when the pH of the solution reaches a value strictly below 4, preferably below 3, for example close to 2, the pH value which allows total, or even virtually total but sufficient, acidification of the soaps and other salts present in the medium and which might result in foaming during the subsequent distillation.

After this acidification step, the formation of an upper phase is generally observed, which upper phase mainly comprises free fatty acids, as well as traces of fatty acid esters. The medium can then be advantageously and preferably subjected, although this step is not obligatory, to a phase separation step (for example decantation, centrifugation, aspiration, withdrawal, or any other technique known by the skilled in the art) in order to separate the esters possibly present, and also the free fatty acids originating from the fatty acid salts after acidification.

Likewise, in cases where insoluble salts are present, a filtration step can be envisaged although this does not represent a preferred variant of the process of the invention.

The acidified solution comprises an amount of glycerol of generally between 30% and 99% by weight relative to the total weight of the acidified reaction crude, more frequently between 50% and 95% by weight of glycerol relative to the total weight of the acidified reaction crude. In addition, the acidified solution may contain methanol, in more or less large amounts, and water, also in more or less large amounts.

In addition, and as indicated above, the glycerol phase generally contains greater or lesser amounts of fatty acid salts, commonly referred to as "soaps". Acidification of this glycerol phase also allows for the transformation of these soaps into free fatty acids (FFA). Now it has been found, and this is still another advantage linked with the use of at least one sulfonic acid, preferably at least one alkane sulfonic acid, preferably methane sulfonic acid, that the acid number (IA) of the glycerol phase, after the acidification step with at least one sulfonic acid according to the invention to eliminate these and FFA, is weaker than when another acid is used.

The resulting benefit is quite significant, considering that this acidified glycerol phase, after removal of the FFA, must be neutralized at neutral pH (about pH=7) before distillation. This neutralization may be carried out according to any means known per se, for example using a base, preferably a strong base, preferably sodium hydroxide or potassium hydroxide. A lower acid number, thanks to prior acidification with at least one sulfonic acid, thus leads to a smaller amount of base which is necessary for the neutralization and therefore the formation of a smaller amount of salts.

Thus, this glycerol-rich acidified phase is then neutralized (at a pH of approximately 7) by means of at least one base, preferably at least one strong base, such as sodium hydroxide or potassium hydroxide. This neutralized solution can then be used in the glycerol distillation step, after distillation of the methanol and water, as indicated below.

The neutralization of the acid phase has consequences on the nature of the medium which is intended to be distilled. Indeed, during this neutralization step, the acid species are neutralized in the form of salts in a glycerol-rich medium.

The inventors have discovered, surprisingly, that the various alkali metal and/or alkaline-earth metal salts present in this phase thus neutralized and intended to be distilled are much more soluble in glycerol when the neutralization has been carried out on a medium acidified beforehand using at least one sulfonic acid, in particular at least one alkane sulfonic acid, more particularly methane sulfonic acid, whereas the same salts are much less soluble when the acidification has been carried out with other acids, in particular strong inorganic acids commonly used in the field, such as sulfuric acid, hydrochloric acid or phosphoric acid.

In addition, the abovementioned salts in the form of sulfonates, preferably alkane sulfonates, more preferably methane sulfonates, have been found to be much more soluble than the sulfates, chlorides and other phosphates, not only in glycerol, but also in glycerol/water mixtures, whatever the glycerol/water ratio and whatever the temperature, in particular whatever the temperature included in the temperature range at which the distillation column operates.

This is all the more notable since distillation operations are very sensitive to the solid impurities present in distillation equipment and in particular in the distillation reboiler (or bottom), but also in the distillation column. As it happens, the temperature and glycerol/water concentration gradients vary along the distillation column.

The acidification with at least one sulfonic acid, preferably at least one alkane sulfonic acid, and more preferably with methane sulfonic acid, offers the advantage of better solubility of the salts, in particular of the sodium and/or potassium salts present in the glycerol, whatever the glycerol/water gradient, which means that the solubility of the salts is higher not only in the reboiler, but also throughout the height of the column.

This advantage of sulfonic acid compared with the other strong acids commonly used thus makes it possible to avoid the formation of solid deposits which can cause disruptions of the streams, in particular in the distillation column itself, and consequently lead to pressure drops, or even risks of clogging, deposits, etc.

In addition, this greater solubility of the sulfonic acid salts in the phase comprising glycerol, and in particular in the reboiler, at the bottom of the column, makes it possible to continue the distillation operation to a more advanced degree, and thus to further improve the distillation yield. Another advantage associated with better solubility of the salts in glycerol is the reduction of the risk of clogging in the bottom of the column, where the glycerol/water mixtures are the most concentrated in terms of glycerol. The overall yield of the distillation is thus greatly improved.

The greater solubility of the salts in the medium to be distilled can also make it possible to envisage a substantial decrease in the number of theoretical plates of the column and, consequently, the physical height of the column, just as it can make it possible to substantially reduce the amount of energy used for the total distillation of the glycerol.

Yet another advantage, associated with the acidification with at least one sulfonic acid, of the reaction crude containing the glycerol lies in the fact that there are fewer solid deposits and, consequently, the periods of interruption for cleaning the distillation equipment are further apart in time.

Yet another advantage is that the sulfonates, and in particular the alkane sulfonates and more particularly the methane sulfonates, are highly soluble in an aqueous medium and are biodegradable. The equipment is consequently easier to clean and, as a result, requires much smaller volumes of water, and the cleaning effluents are more environmentally friendly.

The glycerol present in the acidified and optionally neutralized solution is then separated from the water and from the residual alcohol used during the transesterification reaction. This separation can be carried out according to any method known to those skilled in the art, and preferably by distillation. During this distillation operation, the alcohol, generally methanol, is first of all distilled, followed by the water and, finally, the glycerol. The distillation of the glycerol is generally carried out under reduced pressure, in particular in order to minimize the risks of decomposition of said glycerol at high temperature, for example approximately 10 mbar (approximately 1 kPa), the boiling point of the glycerol then being approximately 160° C., or else between 15 mbar and 150 mbar (between 1.5 kPa and 15 kPa), the boiling point of the glycerol then being between approximately 160° C. and approximately 280° C.

According to another aspect, the present invention relates to an improved process for recovering glycerol from a reaction crude resulting from the triglyceride transesterification reaction, comprising at least the following steps:

a) provision of a basic reaction crude which is rich in glycerol and also contains water and an alcohol, for example methanol;
b) optional separation of the solid impurities;
c) acidification of the reaction crude resulting from step a), with at least one sulfonic acid, to a pH value less than or equal to 4, preferably less than or equal to 3, for example of about 2;
d) optional decanting and separation of the phase rich in glycerol and of the phase rich in free fatty acids and in fatty acid esters;
e) neutralization to a pH of approximately 7, using a base, for example a strong inorganic base, preferably chosen from sodium hydroxide and potassium hydroxide;
f) distillation of the alcohol and of the water;
g) distillation of the glycerol, preferably under reduced pressure;
h) recovery of the glycerol distilled.

According to one variant of the improved process for recovering glycerol, step f) of distillation of the methanol and of the water can be carried out before the neutralization step e). It is also possible to carry out the distillation of the methanol, then to perform the neutralization step, and to conduct the step of distillation of the water and then of the glycerol.

According to yet another aspect, the present invention relates to a combined process for preparing, on the one hand, fatty acid esters or mixtures of fatty acid esters and, on the other hand, glycerol, comprising at least the following steps:

1) provision of triglycerides of vegetable and/or animal origin,
2) transesterification, in a basic medium, of said glycerides, in the presence of at least one alcohol comprising from 1 to 10 carbon atoms, preferably from 1 to 5 carbon atoms, preferably in the presence of methanol, so as to obtain, on the one hand, a phase rich in fatty acid esters or mixtures of fatty acid esters and, on the other hand, a phase rich in glycerol,
3) separation of the phases rich in esters and rich in glycerol, for example by decanting,
4a) recovery of the fatty acid esters and mixtures of fatty acid esters, after acidification, with at least one sulfonic acid, of the phase comprising said fatty acid esters and mixtures of fatty acid esters, and
4b) recovery of the glycerol according to the process described above, step a) to step h), comprising the acidification of the phase comprising the glycerol with at least one sulfonic acid.

This process enables the combined production of both, on the one hand, highly pure glycerol and, on the other hand, fatty acid esters, from oils, in particular from vegetable or animal oils which contain large amounts of triglycerides.

This process is characterized in that it uses at least one sulfonic acid, preferably at least one alkane sulfonic acid and more preferably methane sulfonic acid, both for the acidification of the phase rich in fatty acid esters and for the acidification of the phase rich in glycerol. The use of the same acid for the acidification of the abovementioned two phases has, inter alia, the advantage of greater simplicity of implementation of the industrial operation, the advantage of having a non-corrosive, biodegradable and environmentally friendly acid, and the advantage of solubilizing the salts present in the phase rich in glycerol, making it possible to conduct the final distillation of glycerol under more economical conditions, as has been explained above in the description.

The highly pure distilled glycerol thus obtained can, for example, be used as it is as a solvent, as a component of sanitary or cleaning formulations, or else as a synthesis precursor or intermediate in numerous fields of application, for instance the preparation of pharmaceutical and veterinary products, of cosmetic products, of phytosanitary products, and the like.

The fatty acid esters and mixtures of fatty acid esters may have, for their part, numerous applications, and for example can be used as solvents, surfactants, monomer precursors, fatty alcohol precursors, or lubricants, or else as constituents of biodiesel, i.e. for the manufacture of diesel-type fuel comprising a more or less large amount of compounds of renewable origin, such as diesel fuel corresponding to the European standard.

The following examples illustrate the present invention without, however, limiting the scope thereof defined by the claims which follow.

EXAMPLE 1

Solubilities of the Sodium Salts in Glycerol 30 g of glycerol/water mixture are placed in a 50 mL three-necked flask equipped with a magnetic stirrer, with a condenser and with a temperature probe. The salt to be tested is then added in portions of approximately 0.1 g until undissolved crystals appear (saturation of the medium). The percentage of dissolved salt is calculated according to the following formula:

% dissolved salt=$w/(W+w)$ where W represents the weight of glycerol/water mixture, and w represents the weight of salt introduced.

The salts tested for their solubility in glycerol/water mixtures are the sodium salts of sulfuric ($pK_a$=−9), hydrochloric ($pK_a$=−6.3), acetic ($pK_a$=+4.75) and methane sulfonic ($pK_a$=−1.9) acids.

It could thus be observed that the maximum amount, at 20° C. and at 100° C. respectively, in a 90/10 glycerol/water mixture by weight, of solubilized salt is:
- 2.5% (at 20° C. and at 100° C.) in the case of the salt formed with sulfuric acid (sodium sulfate);
- 8% and 9.4% in the case of the salt formed with hydrochloric acid (sodium chloride);
- 15% and 30% in the case of the salt formed with acetic acid (sodium acetate);
- 15% and 22% in the case of the salt formed with methane sulfonic acid (sodium methane sulfonate).

The maximum solubility of sodium methane sulfonate reaches the value of 22% in a 90/10 glycerol/water mixture by weight, at 100° C.

The above results show that the sodium salts of methane sulfonic acid are 2 to 10 times more soluble in glycerol/water mixtures than, respectively, sodium sulfate and sodium chloride. A solubility of the same order of magnitude is also observed for the salts of methane sulfonic acid and the salts of acetic acid, which is a weak organic acid.

A similar test of glycerol solubility is carried out, however at a temperature of 180° C. (without water). At this temperature of 180° C., it is observed that the maximum quantity of salt solubilized in glycerol is:
- 0.6% for the sodium salt formed with sulfuric acid;
- 7.5% for the sodium salt formed with hydrochloric acid; and
- 26% for the sodium salt formed with methane-sulfonic acid.

EXAMPLE 2

Comparative Study of Various Acids with a Crude Glycerol Phase

For this study, a crude glycerol phase is used. This crude glycerol phase is obtained after trans-esterification with sodium hydroxide of a soybean oil and separation of the phase containing methyl esters (biodiesel).

A quantity of 40 g of this crude glycerol phase is mixed with 4 g of water, at room temperature. Each of the acids to be tested is added over 15 minutes, until a pH value of about 4 is obtained. The reaction mixture is mechanically stirred and allowed to decant for a period of about 4 hours. The upper phase mainly contains free fatty acids (FFA) and traces of esters of fatty acids, whereas the lower phase mainly contains glycerol (glycerol enriched phase).

The following acids are comparatively tested:
- methane sulfonic acid (MSA) at 70% by weight in water (Arkema);
- phosphoric acid ($H_3PO_4$) at 75% by weight in water;
- sulfuric acid ($H_2SO_4$) at 95% by weight in water;
- citric acid (ACi) at 48% by weight in water;
- pure acetic acid (AAc);
- hydrochloric acid (HCl) at 37% by weight in water.

For each test, the following data are measured:
- the added acid quantity, expressed in weight % relative to the mass of crude glycerol phase (40 g);
- the increase of the temperature of the reaction mixture (exotherm, ΔT in ° C.);
- the quantity of insoluble compounds, expressed in weight % relative to the mass of crude glycerol phase (40 g);
- the quantity of obtained glycerol phase, expressed in weight % relative to the total mass of the two phases; and
- the acid number of the glycerol enriched phase.

The acid number (IA) is assessed by neutralization of the acidity of the reaction medium with a strong base (for example potassium hydroxide or sodium hydroxide). The acid number is defined as the quantity (in mg) of KOH necessary to neutralize one (1) gram of sample.

The implemented method is as follows: in a beaker equipped with a stirrer and a pH-measuring electrode (Mettler DG111 for aqueous medium), a sample of exactly about 1 g (mass m) of glycerol enriched phase is introduced, to which are added approximately 50 mL of deionized water. An aqueous sodium hydroxide solution 0.1 mol/L is then added dropwise, with stirring, until pH 12. The equivalence is indicated by a pH jump that gives the equivalent volume v expressed in mL. The acid number (IA), expressed as mg of KOH, is calculated by the following formula:

$$IA = \frac{v \times 0.1 \times 56}{m}$$

where v is in mL, and m in grams.

The results are presented in the following Table 1:

TABLE 1

| acid | MSA | $H_3PO_4$ | $H_2SO_4$ | ACi | AAc | HCl |
|---|---|---|---|---|---|---|
| added quantity (weight %) | 11.5 | 11.3 | 4.5 | 19.5 | 15.0 | 9.3 |
| ΔT (° C.) | 6 | 6 | 12 | 8 | 2 | 8 |
| insoluble compounds (weight %) | 0 | 3.4 | 0 | 0 | 0 | 0 |
| IA (mg of KOH/g) | 1 | 61 | 2 | 37 | 92 | 2 |
| glycerol phase (weight %) | 68 | 63 | 32 | 65 | 64 | 67 |

The amount of added acid is substantially identical for MSA, phosphoric acid and hydrochloric acid. This amount is approximately two times higher for the weak organic acids (citric acid), and two times lower for sulfuric acid. However, with sulfuric acid, the formation of a gel which is detrimental to a good phase separation is observed, and results in a twice lesser amount of recovered glycerol.

In addition, the strong exotherm observed in the test with sulfuric acid can be troublesome at the industrial level, requiring precautions during acidification, including special facilities, e.g. a cooling module.

The amount of insoluble compounds produced during the test with phosphoric acid makes this an unsuitable acid, the insoluble compounds being particularly troublesome, especially during the subsequent glycerol purification step by distillation, as described above.

These results also show that the acid number (IA) of the acidified is glycerol phase is lower in the case of MSA, H$_2$SO$_4$ and HCl. This is a particularly interesting advantage, considering the subsequent neutralization of this glycerol phase with a strong base until pH 7, before distillation.

The use of hydrochloric acid is not required on an industrial scale because of corrosion problems associated with this acid. Moreover, at 37% in water, which represents the maximum attainable concentration, hydrochloric acid contains a very large amount of water, which is weakly interesting on an economical point of view, during the subsequent glycerol distillation.

These results show the great advantage associated with the use of MSA, relative to other acids in industrial processes for production of glycerol from triglycerides, but also in industrial processes for the combined production of biodiesel and glycerol from triglycerides:

- MSA is a weakly corrosive and environmental friendly acid;
- salts formed with this acid are much more soluble in glycerol;
- the amount of MSA necessary to acidify the crude glycerol phase and the exotherm due to acidification are quite comparable with those observed with phosphoric acid, however without generating insoluble compounds;
- the acid number of the enriched glycerol phase is very low, leading to a lower amount of base necessary for the subsequent neutralization and accordingly a smaller amount of neutralization salts, and finally
- a quite important amount of recovered enriched glycerol phase.

MSA thus represents a particularly advantageous alternative, in particular to phosphoric, sulfuric or hydrochloric acids, for the production of glycerol from triglycerides.

The invention claimed is:

1. A process for recovering glycerol resulting from a reaction crude from transesterification of glycerides comprising: adding at least one sulfonic acid during an acidification stage.

2. The process of claim 1, wherein said at least one sulfonic acid corresponds to the general formula R—SO$_3$H, where R represents an alkyl or aryl radical.

3. The process of claim 1, wherein said at least one sulfonic acid corresponds to the general formula R—SO$_3$H, where R represents a linear or branched, saturated hydrocarbon-based chain containing from 1 to 4 carbon atoms.

4. The process of claim 1, wherein said at least one sulfonic acid is methane sulfonic acid (CH$_3$SO$_3$H).

5. The process of claim 1, wherein said at least one sulfonic acid is in anhydrous form or in the form of an aqueous solution comprising from 5% to 90% by weight of sulfonic acid, the rest to 100% consisting of water.

6. The process of claim 1, wherein said at least one sulfonic acid is used for the acidification of a reaction crude from transesterification of glycerides, comprising:
   - glycerol,
   - the alcohol(s) used for the transesterification reaction,
   - optionally water, or traces of water,
   - the basic catalyst(s) (used for the transesterification reaction), possibly in trace form,
   - fatty acid salt(s), possibly in trace form,
   - optionally one or more fatty acid ester(s), possibly in trace form,
   - optionally traces of mono-, di- and/or triglycerides,
   - optionally traces of organic residues other than glycerol,
   - optionally traces of metals.

7. A process for recovering glycerol from a reaction crude resulting from a triglyceride transesterification reaction, comprising at least the following steps:
   a) providing a basic reaction crude which is rich in glycerol and also contains water and an alcohol;
   b) optionally separating the solid impurities;
   c) acidifying the reaction crude resulting from step a), with at least one sulfonic acid, to a pH value less than 4;
   d) optionally decanting and separating the phase rich in glycerol and of the phase rich in free fatty acids and in fatty acid esters;
   e) neutralizing to a pH of approximately 7, using a base;
   f) distilling the alcohol and the water;
   g) distilling the glycerol;
   h) recovering the glycerol distilled.

8. The process of claim 7, wherein the at least one sulfonic acid is methane sulfonic acid.

9. A combined process for preparing, on the one hand, fatty acid esters or mixtures of fatty acid esters and, on the other hand, glycerol, comprising at least the following steps:
   1) providing triglycerides of vegetable and/or animal origin,
   2) transesterifying, in a basic medium, said triglycerides, in the presence of at least one alcohol comprising from 1 to 10 carbon atoms, so as to obtain, on the one hand, a phase rich in fatty acid esters or mixtures of fatty acid esters and, on the other hand, a phase rich in glycerol,
   3) separating the phases which are, on the one hand, rich in esters and, on the other hand, rich in glycerol,
   4a) recovering the fatty acid esters and mixtures of fatty acid esters, after acidification, with at least one sulfonic acid, of the phase comprising said fatty acid esters and mixtures of fatty acid esters, and
   4b) recovering the glycerol according to the process of claim 7, comprising the acidification of the phase comprising the glycerol with at least one sulfonic acid.

10. The process of claim 9, wherein said at least one sulfonic acid of step 4b is methane sulfonic acid.

11. The process of claim 9, wherein said at least one sulfonic acid of step 4a is methane sulfonic acid.

12. The process of claim 1, wherein the glycerides are triglycerides of vegetable and/or animal origin.

13. The process of claim 1, wherein the at least one sulfonic acid comprises an alkane sulfonic acid.

14. The process of claim 2, wherein R represents an alkyl radical.

15. The process of claim 5, wherein said aqueous solution comprises from 10% to 80% by weight of sulfonic acid.

16. The process of claim 15, wherein said aqueous solution comprises from 15% to 75% by weight of sulfonic acid.

17. The process of claim 7, wherein the alcohol comprises methanol.

18. The process of claim 7, wherein the step for acidifying the reaction crude, the pH value is less than 3.

19. The process of claim 18, wherein the step for acidifying the reaction crude, the pH value is about 2.

20. The process of claim 7, wherein the base comprises a strong inorganic base.

21. The process of claim 20, wherein the strong inorganic base comprises sodium hydroxide or potassium hydroxide.

22. The process of claim 9, wherein the at least one alcohol comprises methanol.

23. The process of claim 9, wherein the step of separating is carried out by decantation.

24. The process of claim 7, wherein the step for distilling the glycerol is carried out under reduced pressure.

25. The process of claim 7, wherein step f) is carried out before step e).

* * * * *